United States Patent [19]

Kaito et al.

[11] Patent Number: 5,028,780
[45] Date of Patent: Jul. 2, 1991

[54] PREPARATION AND OBSERVATION METHOD OF MICRO-SECTION

[75] Inventors: Takashi Kaito; Tatsuya Adachi, both of Tokyo, Japan

[73] Assignee: Seiko Instruments, Inc., Tokyo, Japan

[21] Appl. No.: 444,716

[22] Filed: Dec. 1, 1989

[30] Foreign Application Priority Data

Dec. 1, 1988 [JP] Japan .................... 63-304369

[51] Int. Cl.$^5$ ............................ H01J 37/30
[52] U.S. Cl. .................... 250/307; 250/309; 250/492.1; 250/492.2; 250/492.3
[58] Field of Search ............ 250/307, 309, 492.21, 250/491.1, 492.2, 492.3, 492.1; 156/643, 662, 657; 357/71 R; 427/38; 437/195, 189

[56] References Cited

U.S. PATENT DOCUMENTS

| | | | |
|---|---|---|---|
| 4,418,283 | 11/1983 | Trotel | 250/492.2 |
| 4,457,803 | 7/1984 | Takigawa | 250/492.21 |
| 4,503,329 | 3/1985 | Yamaguchi et al. | 250/309 |
| 4,683,378 | 7/1987 | Shimase et al. | 250/491.1 |
| 4,733,074 | 3/1988 | Kato et al. | 250/492.2 |
| 4,900,695 | 2/1990 | Takahashi et al. | 357/71 R |
| 4,908,226 | 3/1990 | Kubena et al. | 250/492.3 |

Primary Examiner—Jack I. Berman
Assistant Examiner—Kiet T. Nguyen
Attorney, Agent, or Firm—Spensley Horn Jubas & Lubitz

[57] ABSTRACT

The method of preparing and observing a microsection utilizes a focused ion beam device composed of an ion tube for producing a scanned and focused ion beam, a sample stage including an XY displacement mechanism and an inclination mechanism, a gas gun for injecting deposition material gas onto a surface of a sample and a secondary charged particle detector such that the focused ion beam device has three functions, i.e., a scanning ion microscope function, a maskless etching function and a maskless deposition function. The method is directed to sequentially carry out highly accurate preparation of a section in a particular area of the sample and observation of the prepared section according to first step of determining a position of the cutting edge on the sample surface by the scanning ion microscope function, a second step of depositing a film locally on an area containing the cutting edge position by the maskless deposition function, a third step of forming a rectangular groove by the maskless etching function such that one sidewall of the rectangular groove is registered with the cutting edge so as to prepare and expose a section, a fourth step of inclining the sample stage to face the section in an observation direction, and a fifth step of carrying out observation of the section in the formed groove by the scanning ion microscope function.

3 Claims, 1 Drawing Sheet

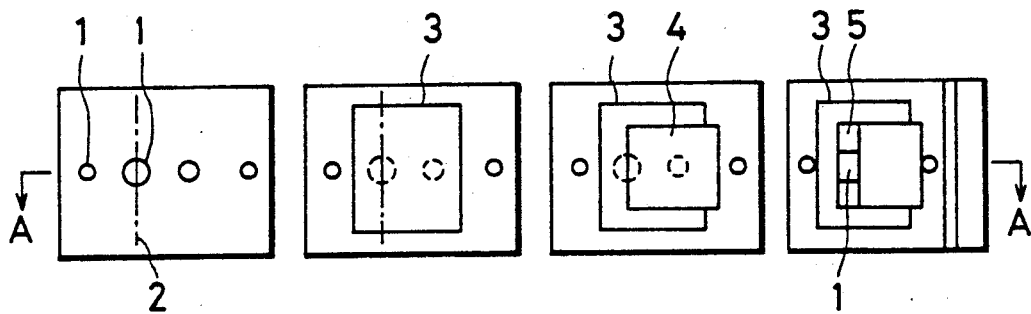
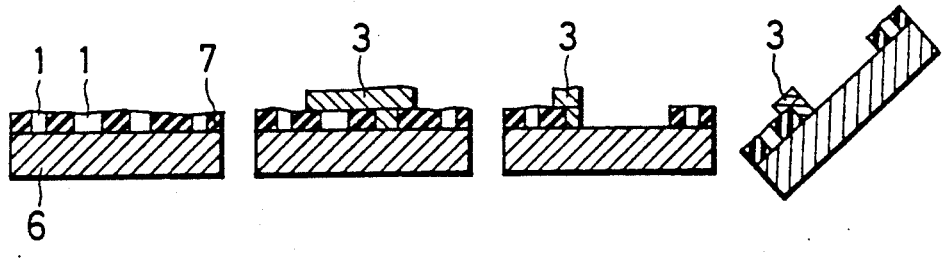
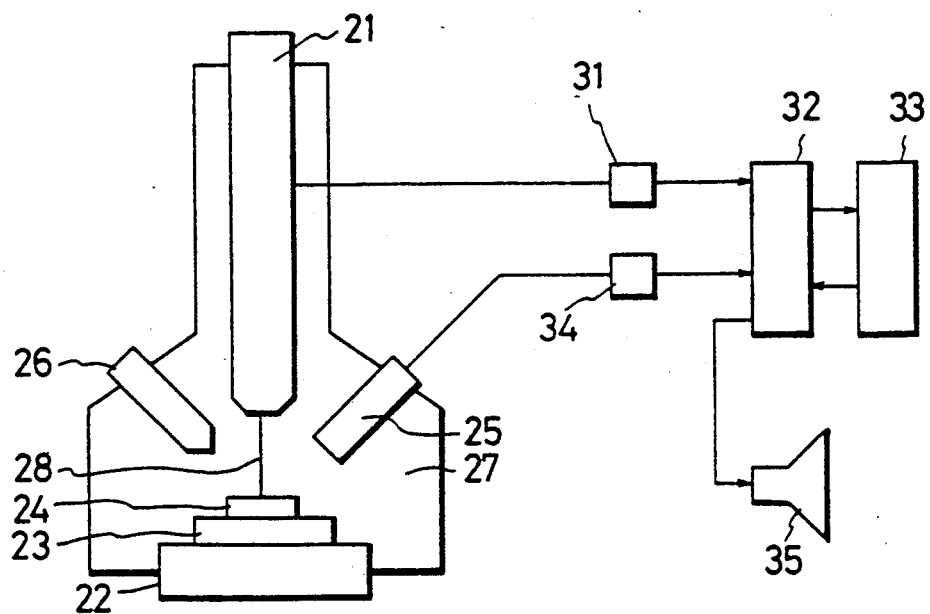

PREPARATION AND OBSERVATION METHOD OF MICRO-SECTION

BACKGROUND OF THE INVENTION

The present invention relates to a method of preparing and observing a cross section of a particular spot of a semiconductor device for failure analysis.

FIG. 3 shows a schematic side view of a focused ion beam device, which performs a maskless processing operation and is used for research and development of the most advanced semiconductor devices and fabrication processes. This device is equipped to perform several functions such as a scanning ion microscope function, a maskless etching function and a maskless deposition function.

In view of these functions, this device can be used for observation of a section of a semiconductor device. Namely, a particular cutting edge position is determined by the scanning ion microscope function which is one of the features of this device, then a rectangular groove is formed in a particular spot area by the maskless etching function such that one side of the rectangle is aligned along the cutting edge position to thereby expose a desired section to be observed, and thereafter the sample is inclined so that the section faces toward the incident ion beam to thereby observe the section, again by the scanning ion microscope function.

However, in this method, when preparing a section for observing a contour of an uneven area containing a trench, etc., sputtered material may be redeposited in the trench during the maskless etching, or the uneven contour may effect the prepared section by forming stripes thereon. This results in the drawback that an accurate image of the section cannot be obtained.

SUMMARY OF THE INVENTION

An object of the present invention is to prepare and observe a section in a manner which effectively eliminates the above-noted drawbacks.

The invention is based on applicants' discovery that a clear-cut section can be formed by provisionally leveling a particular spot area of a sample surface before the cutting of a section by the FIBCVD process (focused ion beam chemical-vapor-deposition process).

In order to realize the above object, according to the present invention, the method of preparing and observing a micro-section utilizes a focused ion beam device composed of a focused ion beam tube having switching means for switching the ion beam current, a sample stage including an XY displacement mechanism and an inclination mechanism, a gas gun for injecting deposition material gas onto a surface of a sample and a secondary charged particle detector such that the focused ion beam device can perform three functions, i.e., a scanning ion microscope function, a maskless etching function and a maskless deposition function. The method is performed to sequentially carry out highly accurate preparation of a section in a particular area of a sample and observation of the prepared section according to the following steps:

a first step of determining a position of a cutting edge on the sample surface by the scanning ion microscope function;

a second step of depositing a film locally on an area containing the cutting edge position by the maskless deposition function;

a third step of forming a rectangular groove by the maskless etching function such that one sidewall of the rectangular groove is registered with the cutting edge so as to prepare and expose a section;

a fourth step of inclining the sample stage to face the section in an observation direction; and a fifth step of carrying out observation of the section in the formed groove by the scanning ion microscope function.

Preferably in the third step of forming the rectangular groove to expose the section, the switching means is operated to provide firstly a high current ion beam for coarsely forming a groove, and then to provide an intermediate current ion beam for finishing the section. Further in the fifth step, a low current ion beam is provided for observation of the finished section.

Moreover, after finishing one cycle of the first to fifth steps, the sidewall of the rectangular groove formed in the third step may be sliced, using the maskless etching function, to prepare a new section adjacent to the previously formed section, and thereafter the fourth and fifth steps are carried out to effect observation of the new section. The slicing can be carried out repeatedly to produce a plurality of images of adjacent sections. These section images are inputted into an image storage and processing device to thereby synthesize the section images in the form of a three dimensional display of the micro-sections.

According to the invention, a film is deposited using the maskless deposition function on a particular area of the sample surface containing a cutting edge position to level an uneven face. Consequently, the method can avoid redeposition of sputtered material into cavities such as a trench and deposition of stripe patterns on the section due to surface unevenness, thereby providing an accurate and clear-cut section. Further, the cutting edge position can be sequentially shifted to effect slicing to obtain successive sections. The image of these sections is processed to produce a three-dimensional image of the particular spot.

BRIEF DESCRIPTION OF THE DRAWINGS

FIGS. 1A through 1D are top plan views illustrating successive stages of the inventive method when applied to observe a trench of an IC chip, wherein FIG. 1A shows a cutting edge position of the IC chip by a dot and chain line; FIG. B shows an area containing the trench and being deposited with a film, as indicated by hatching, by a FIBCVD process; FIG. 1C shows a rectangular groove formed by an etching process such that one side of the rectangular groove registers with the cutting edge position; and FIG. 1D shows an observation arrangement such that a sample stage is inclined (right side up in the Figure) to face an exposed section to the ion beam irradiation direction for observation.

FIG. 2A through 2D are sectional views of the corresponding FIGS. 1A through 1D taken along line A—A.

FIG. 3 is a schematic elevational view showing a focused ion beam device and an image processing circuit used in the practice of the inventive method.

DESCRIPTION OF THE PREFERRED EMBODIMENTS

The inventive method for preparation and observation of a micro-section of a sample utilizes the combination of a focused ion beam device and an image processing circuit. Referring to FIG. 3, the focused ion beam device is composed of an ion beam tube 21 for producing a scanned ion beam 28 to irradiate a sample 24 held in sample holder 23 of a sample stage 22 which is displaceable in X and Y directions and can be inclined relative to the axis of ion beam 28. The ion beam tube 21 is disposed in a vacuum chamber 27. A gas gun 26 is also disposed in vacuum chamber 27 for directing a deposition material in gas form onto a surface of the sample 24 such that the gas is selectively deposited thereon upon irradiation by the scanned ion beam to locally form a film, thereby effecting a maskless deposition function. A secondary charged particle detector 25 is disposed in vacuum chamber 27 to detect secondary charged particles released from the surface of sample 24 upon irradiation by the scanned ion beam 28 to thereby effect a scanning ion microscope function. The ion beam tube 21 can be operated alone to locally direct the scanned ion beam to selectively sputter the sample surface, to thereby effect a maskless etching function. The ion beam current can be switched between different current levels.

A scanning control unit 31 is connected to ion beam tube 21 to control the scanning of the ion beam 28, and an amplifier 34 is connected to the detector 25 to amplify a detection signal therefrom. An image retrieving and reproducing control unit 32 is connected to the scanning control unit 31 and to the amplifier 34 for processing the detection signal to form an image. A display unit 35 is connected to display the image and an image memory unit 33 is connected to store the image.

Next, the inventive method will be described step by step when applied for the observation of a trench formed in a sample of an IC chip which is mounted in the vacuum chamber of the focused ion beam device.

Referring to FIGS. 1A and 2A, a cutting edge position is determined, as indicated by the chain line 2, by performance of the scanning ion microscope function over a trench 1 formed in a surface of an IC chip sample which is composed of an Si substrate 6 and an $SiO_2$ layer 7.

Next referring to FIGS. 1B and 2B, a film 3 is deposited on the sample surface, by performing a maskless deposition function, i.e., a focused ion beam chemical-vapor-deposition (FIBCVD) process, within an area containing the particular trench 1 to be observed, as indicated by hatching in FIG. 2B. The FIBCVD process is carried out such that the gas gun 26 is operated to form a layer of the deposition material gas and the ion tube 21 is concurrently operated to irradiate the ion beam 28, accelerated by an energy of 20-30 KeV, locally onto the sample surface to selectively deposit a film 3 within the locally irradiated area. In this embodiment, the deposition material gas is composed of $W(CO)_6$ to form a tungsten film. Other material gas can be used to form a metal film of different material to carry out the inventive method. The deposition of film 3 can fill cavities including trench 1 to level the top face of the sample within the area.

Referring to FIGS. 1C and 2C, after the deposition of film 3, a cavity 4 of rectangular shape is formed by performance of a maskless etching function such that one side of the rectangular shape registers with the cutting edge position 2 to expose a section 5 to be observed. As described above, prior to this masking step, the cavity of the trench 1 has been filled by the deposited film 3 and the top surface of the sample has been leveled, thereby avoiding redeposition of sputtered material into the cavity and deposition of a stripe pattern on the section due to unevenness of the sample surface, which undesirable results would be caused in the prior art method which does not carry out deposition of a film prior to preparation of the section. Consequently, an accurate shape of the section can be realized.

Cavity 4 is formed in two steps such that firstly a coarse grooving is carried out and then a finishing process is carried out, thereby achieving a fast and accurate preparation of the section. The coarse grooving or sputtering is carried out with a relatively high current ion beam. For example, a gallium ion beam of 6 nA, 30 KeV is utilized to sputter Al, $SiO_2$ or Si at the rate of about 0.6-0.7 sec/$\mu m^3$. The finishing process uses an intermediate current ion beam (2 nA-30 pA) to irradiate the sputtered cavity wall to thereby form the section 5 with a steep sidewall.

Lastly, referring to FIGS. 1D and 2D, the sample stage is inclined at an appropriate angle to face the prepared section of the sample to the ion beam irradiation direction. A relatively low current ion beam (30-2 pA) is scanned along the prepared section to observe the same by the scanning ion microscope function. The observation result has been found to be excellent and has substantial contrast as compared to a scanning electron microscope.

In order to obtain a three-dimensional display image based on several adjacent sections, the above-described steps are carried out repeatedly. Namely, the cutting edge position 2 is shifted slightly and the slicing process is carried by the maskless etching function to expose successive new sections. Each new section is inclined to face to the ion beam irradiation direction. Then, the observation is carried out for the new section by the scanning ion microscope function. These steps are repeated an appropriate number of times. The thus obtained slice images are stored in image memory unit 33 and are lastly reproduced in the form of a three-dimensional display image.

According to the present invention, as described above, film 3 is deposited on a particular area containing the cutting edge position 2 prior to the preparation of the section, so that a trench cavity, etc., is filled by the film and the unevenness of the sample surface is eliminated by leveling the same, thereby avoiding redeposition of sputtered material into the cavity and deposition of a strip pattern on the section due to the effects of surface unevenness. Accordingly, a clear-cut section image can be obtained to show the surface contour and the trench configuration.

This application relates to subject matter disclosed in Japanese Patent Application No. 63-304369, filed on Dec. 1, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of preparing and observing a micro-section utilizing a focused ion beam device, which device includes a focused ion beam tube for producing a focused ion beam, a sample stage including an XY displacement mechanism and an inclination mechanism for supporting a sample for irradiation by the focused ion beam, a gas gun disposed for injecting deposition material gas onto a surface of a sample supported by the sample stage; and a secondary charged particle detector disposed for detecting secondary charged particles emitted by the sample, the focused ion beam device being constructed to perform three functions, which are a scanning ion microscope function, a maskless etching function, and a maskless deposition function said method comprising:

a first step of causing the device to perform the scanning ion microscope function for determining a position of a cutting edge on the surface of a sample supported by the sample stage;

a second step of causing the device to perform the maskless deposition function for depositing a film locally on an area containing the cutting edge position;

a third step of causing the device to perform the maskless etching function for forming a rectangular groove having one sidewall which is registered with the cutting edge so as to prepare and expose a section of the sample;

a fourth step of inclining the sample stage to orient the section in an observation direction; and a fifth step of causing the device to perform the scanning ion microscope function for carrying out observation of the section in the formed groove.

2. The method according to claim 1, wherein: the ion beam tube includes switching means for switching the current level of the ion beam; said third step is carried out by operating the switching means to firstly produce a high current ion beam for coarsely forming a groove, and to then produce an intermediate current level ion beam for finishing the section; and said fifth step is carried out by operating the switching means to produce a low current level ion beam for observation of the finished section.

3. A method for observing a section of a sample, the sample having an outer surface and the section being along a plane which intersects the outer surface along a line of intersection, comprising:

forming a film upon the outer surface, so that the film extends across the line of intersection, by irradiating the surface with a focussed ion beam and directing a deposition material gas onto the outer surface; etching the sample and the film along said plane, for exposing the sample and film along said plane, by irradiation with a focussed ion beam; and observing at least part of said plane by irradiating said plane with a focussed ion beam and detecting secondary charged particles released from the sample.

* * * * *